US012611325B2

(12) United States Patent
Gekhter et al.

(10) Patent No.: US 12,611,325 B2
(45) Date of Patent: Apr. 28, 2026

(54) EXTERNAL PENILE SUPPORT DEVICE

(71) Applicant: Global Life Technologies, LLC, Skokie, IL (US)

(72) Inventors: Vladimir Gekhter, Skokie, IL (US); Gary Little, West Dundee, IL (US)

(73) Assignee: Global Life Technologies, LLC, Skokie, IL (US)

( * ) Notice: Subject to any disclaimer, the term of this patent is extended or adjusted under 35 U.S.C. 154(b) by 1057 days.

(21) Appl. No.: 17/715,788

(22) Filed: Apr. 7, 2022

(65) Prior Publication Data

US 2022/0323250 A1      Oct. 13, 2022

Related U.S. Application Data

(60) Provisional application No. 63/171,994, filed on Apr. 7, 2021.

(51) Int. Cl.
*A61F 5/41* (2006.01)

(52) U.S. Cl.
CPC ........... *A61F 5/41* (2013.01); *A61F 2005/411* (2013.01)

(58) Field of Classification Search
CPC .............................. A61F 5/41; A61F 2005/411
See application file for complete search history.

(56) References Cited

U.S. PATENT DOCUMENTS

| | | | | |
|---|---|---|---|---|
| 4,449,521 | A | 5/1984 | Panzer | |
| 5,800,340 | A * | 9/1998 | Gekhter | A61F 5/41 |
| | | | | 600/39 |
| 7,578,785 | B2 * | 8/2009 | Suchy | A61H 1/0218 |
| | | | | 600/38 |
| 8,394,011 | B2 | 3/2013 | Gekhter | |
| 2007/0038019 | A1 | 2/2007 | Weng | |
| 2008/0076964 | A1 | 3/2008 | Jared | |
| 2010/0130816 | A1 * | 5/2010 | Gekhter | A61F 5/41 |
| | | | | 600/39 |

* cited by examiner

*Primary Examiner* — Samuel G Gilbert
(74) *Attorney, Agent, or Firm* — Michael Best & Friedrich LLP

(57) ABSTRACT

An expandable external penile support device for using on a penis having a base, a distal end, and a variable diameter, the expandable external penile support device includes a base ring configured to be positioned adjacent the base of the penis, a latch coupled to the base ring, and a support structure removably coupled to the base ring by the latch. The support structure includes a support member engageable with the distal end of the penis and having an expandable diameter that varies according to the diameter of the penis. The support member also includes at least one connection end. At least one support rod extends between the latch and the support member. Each of the at least one support rods includes a resilient core having a first end proximate the latch and a second end proximate the support member, a sleeve surrounding at least the second end of the resilient core, an end cap engaged with the sleeve such that the end cap encapsulates the second end of the resilient core, wherein the end cap is coupled to the connection end of the support member.

17 Claims, 5 Drawing Sheets

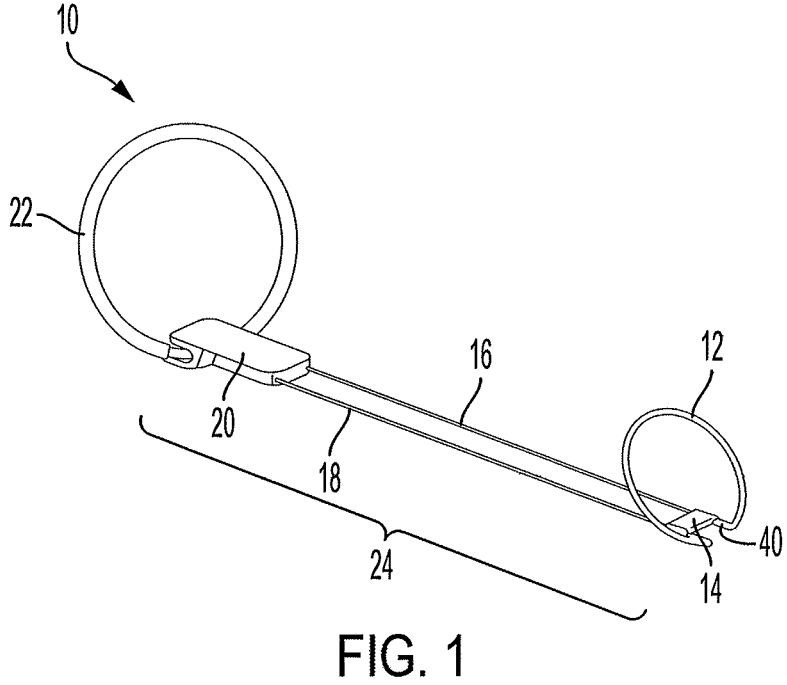
FIG. 1
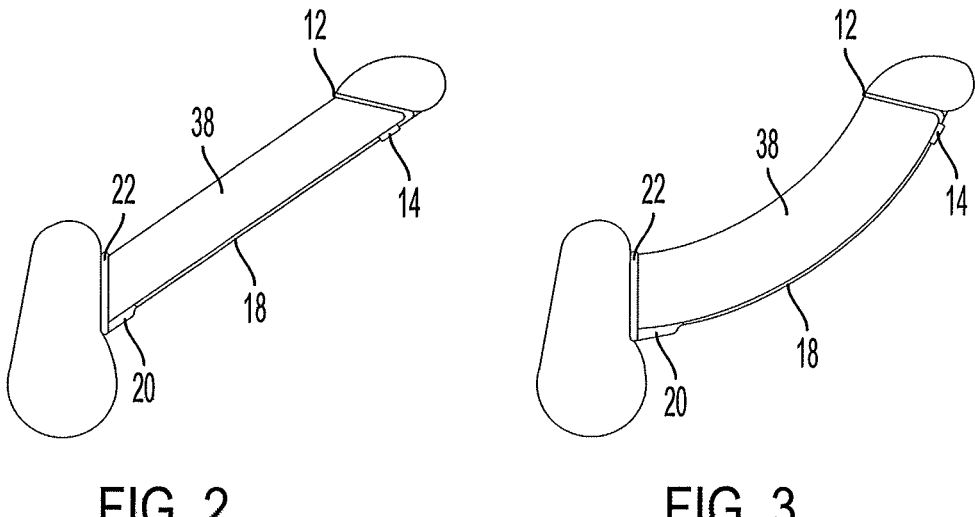
FIG. 2                    FIG. 3

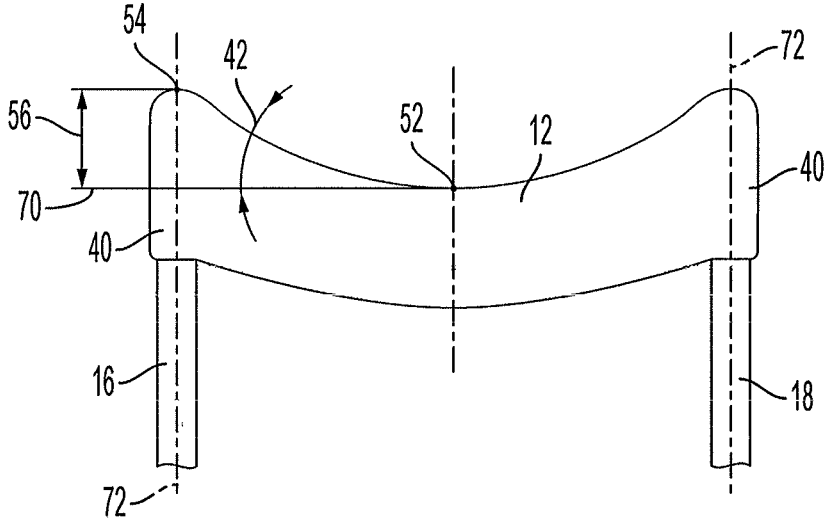
FIG. 11
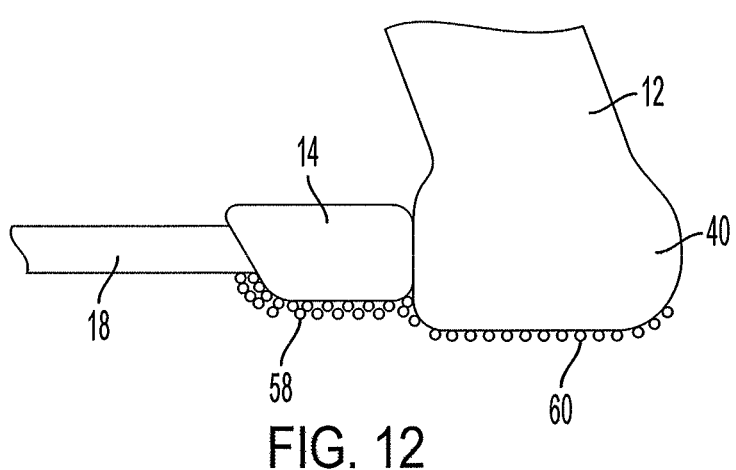
FIG. 12
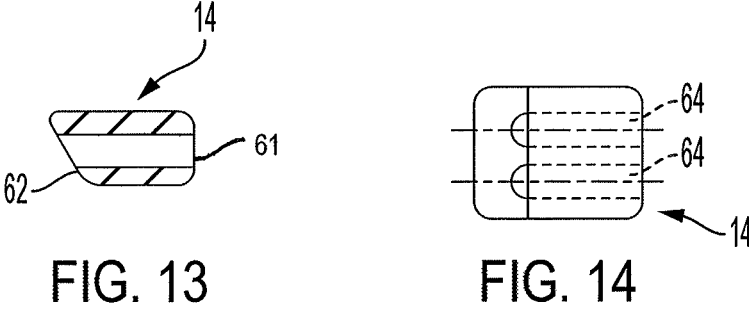
FIG. 13
FIG. 14

EXTERNAL PENILE SUPPORT DEVICE

CROSS-REFERENCE TO RELATED APPLICATION

This application claims the benefit of and priority to U.S. Provisional Patent Application No. 63/171,994 filed Apr. 7, 2021, the entire contents of which are hereby incorporated by reference.

FIELD OF THE INVENTION

The disclosure resides in the field of sexual aid for men, more particularly in the ability for men to perform intercourse with a weak erection or without an erection at all without the need for medications while being able to overcome the discrepancies in men and women anatomy of private parts.

BACKGROUND

Erectile dysfunction, sometimes called "impotence," is the repeated inability to achieve or maintain an erection firm enough for sexual intercourse. Impotence may also be used to describe other problems that interfere with sexual intercourse and reproduction, such as lack of sexual desire and problems with ejaculation or orgasm. Erectile dysfunction, or ED, can be a total inability to achieve erection, an inconsistent ability to do so, or a tendency to sustain only brief erections. These variations make defining ED and estimating its incidence difficult. Estimates range from 15 million to 30 million in US and over 150 million worldwide, depending on the definition used. The treatments for impotence include medications, vacuum devices, injectable drugs and implant surgeries. Perhaps the most publicized advance was the introduction of the oral drug sildenafil citrate (Viagra®) in March 1998. Viagra® fails to work for three out of 10 men, according to Pfizer, or cannot be used by 50% of men with erectile dysfunctions due to side effects, according to other medical sources. In older men, ED usually has a physical cause, such as disease, injury, or side effects of drugs. Any disorder that causes injury to the nerves or impairs blood flow in the penis has the potential to cause ED. Impotence increases with age: about 5 percent of 40-year-old men and between 15 and 25 percent of 65-year-old men experience ED. Medications produce many undesirable side effects including death. Vacuum devices are clumsy and inconvenient; surgeries are painful, ineffective, expensive, and even dangerous.

Some prior external penile support devices do not find broad applications in treatment of impotence due to great discomfort for the users and difficulties to adjust for the variety of men's private parts. Another problem with some prior external penile support devices is that they include a number of parts, which often become disassembled during use, possibly resulting in injury to both the user and the user's partner. Additionally, some prior penile supports are bulky, having large cross-sections that do not accommodate for changes in penis size during erection. Another problem is that some prior devices are ineffective in retaining their contoured shape or are being expensive to manufacture due to their relatively complex designs.

SUMMARY OF THE INVENTION

In one aspect, an expandable external penile support device for using on a penis having a base, a distal end, and a variable diameter. The expandable external penile support device including a base ring configured to be positioned adjacent the base of the penis, a latch coupled to the base ring, and a support structure removably coupled to the base ring by the latch. The support structure includes a support member engageable with the distal end of the penis and having an expandable diameter that varies according to the diameter of the penis. The support member also including at least one connection end. At least one support rod extends between the latch and the support member, each of the at least one support rods including a resilient core having a first end proximate the latch and a second end proximate the support member, a sleeve surrounding at least the second end of the resilient core, an end cap engaged with the sleeve such that the end cap encapsulates the second end of the resilient core, wherein the end cap is coupled to the connection end of the support member.

In another aspect, an expandable external penile support device for use on a penis includes a base, a distal end, and a variable diameter. The expandable external penile support device including a base ring configured to be positioned adjacent the base of the penis, a pair of resilient rods, each having a first end and second end, the base ring removably coupled to the first ends of the support rods, and a support member configured to engage with the distal end of the penis and having an expandable diameter that varies according to the diameter of the penis. The support member has a first connection end coupled to the second end of one of the resilient rods and a second connection end coupled to the second end of the other of the resilient rods. The expandable external penile support device further including a lock member slidable supported by the resilient rods to adjust tension of the support member on the penis. Each of the first and second connection ends includes a bottom surface defining a first plane and the lock member includes a bottom surface defining a second plane, and further wherein the second plane is recessed from the first plane.

In yet another aspect, an expandable external penile support device for using on a penis having a base, a distal end, and a variable diameter. The expandable external penile support device including a base ring configured to be positioned adjacent the base of the penis and at least one resilient support rod having a first end and a second end, the base ring removable coupled to the first end of the at least one resilient support rod. The expandable external penile support device further including a support member coupled to the second end of the at least one resilient support rod and configured to engage the distal end of the penis, wherein the support member is a non-metallic member configured to expand in response to the variable diameter of the penis increasing.

Other aspects of the disclosure will become apparent by consideration of the detailed description and accompanying drawings.

BRIEF DESCRIPTION OF THE DRAWINGS

FIG. 1 is a perspective view of an external penile support device (EPSD).

FIG. 2 is a side view of the EPSD of FIG. 1 on a penis.

FIG. 3 is a side view of the EPSD of FIG. 1 on a penis of a differing shape.

FIG. 11 is a top view of a portion of the EPSD of FIG. 1 including the support member in a generally flat configuration.

FIG. 12 is a side view of a portion of the EPSD of FIG. 1 including a slidable lock coupled to support rods adjacent the support member.

FIG. 13 is a side cross-sectional view of the slidable lock of FIG. 12.

FIG. 14 is a bottom view of the slidable lock of FIG. 12.

Figure 4:
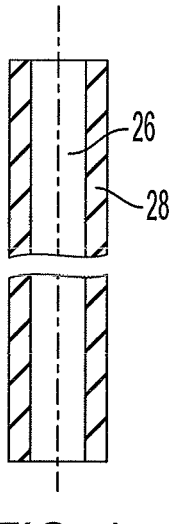
FIG. 4 is a partial cross-sectional view of a support rod of the EPSD of FIG. 1.
Figure 5:
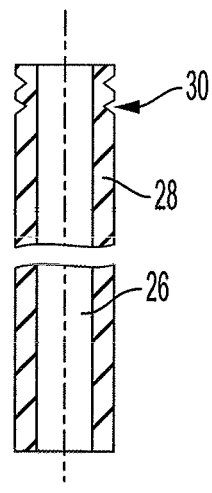
FIG. 5 is a partial cross-sectional view of the support rod of FIG. 4 including notches.

Before any embodiments of the disclosure are explained in detail, it is to be understood that the disclosure is not limited in its application to the details of construction and the arrangement of components set forth in the following description or illustrated in the following drawings. The disclosure is capable of supporting other embodiments and being practiced or being carried out in various ways. Also, it is to be understood that the phraseology and terminology used herein is for the purpose of description and should not be regarded as limiting. Terms of degree, such as "substantially," "about," "approximately," etc. are understood by those of ordinary skill to refer to reasonable ranges outside of the given value, for example, general tolerances associated with manufacturing, assembly, and use of the described embodiments.

DETAILED DESCRIPTION

FIG. 1 illustrates an external penile support device (EPSD) 10 according to an embodiment of the disclosure. The EPSD 10 may be placed on the penis to allow men to perform intercourse with no erection or a weak erection without the need for medications, surgeries, and the like. In addition, the EPSD 10 may be used with men suffering from any one of, but not limited to, erectile dysfunction, premature ejaculation, and Peyronie's disease. The EPSD 10 may also be used to overcome discrepancies between men and women's anatomy. The illustrated EPSD 10 includes an expandable support member 12, a slidable lock or lock member 14, resilient support rods 16, 18 upon which the slidable lock 14 is slidable, a latch 20 coupled to the support rods 16, 18, and a base ring 22 coupled to the latch 20. In the illustrated construction, a support structure 24 includes the support member 12, the slidable lock 14, the support rods 16, 18 and the latch 20. The support structure 24 is removably coupled to the base ring 22 by the latch 20.

The EPSD 10 is flexible enough to accommodate both straight and bent penis shafts (FIGS. 2 and 3), yet provide sufficient support to the penis to permit penetration of the penis for purposes of intercourse. In some constructions, the EPSD 10 does not rotate on the penis during use. In other constructions, the EPSD 10 applies uniform pressure to a vein of the penis for optimally stimulating and maintaining an erection. FIG. 2 illustrates the EPSD 10 coupled to a penis 38 with the support rods 16, 18 supporting the penis in a first configuration, and FIG. 3 illustrates the EPSD 10 coupled to the penis 38 with the support rods 16, 18 supporting the penis in a second, bent configuration. The first and second support rods 16, 18 extend between the expandable support member 12 and the latch 20 (described below). Each of the support rods 16, 18 includes a first end removably coupled to the base ring 22 by the latch 20 and a second end coupled to the support member 12. The length of the support rods 16, 18 substantially correspond with the overall length of the penis, and may be custom built, come in a set of standard sizes, or be adjustable to accommodate different penis sizes.

Figure 6:
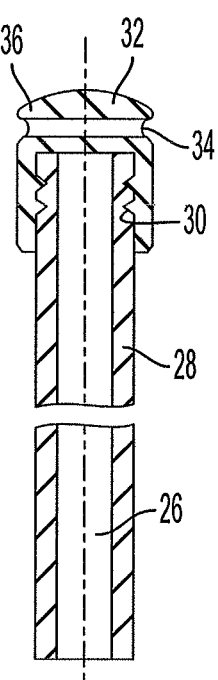
FIG. 6 is a partial cross-sectional view of the support rod of FIG. 5 including an end cap interfacing with the notches to provide a mechanical interlock between the support rod and the end cap.

With reference to FIG. 4, each of the illustrated support rods 16, 18 includes a resilient core 26 (e.g., a Nickel-Titanium alloy wire such as Nitinol™) and a sleeve 28 (e.g., a plastic tubing, a plastic over-mold, etc.) around the resilient core 26. The core 26 is formed from a material that does not deform and recovers to its original shape after bending to any degree. The illustrated sleeve 28 is manufactured from a medical-grade material. In the illustrated embodiment, each of the support rods 16, 18 includes notches 30 formed in the sleeve 28 adjacent an end of the respective support rod 16, 18. As shown in FIG. 6, an end cap 32 includes a circumferential groove 34 and a semi-spherical head 36, and is coupled to the end of the support rod 16, 18. In the illustrated embodiment, the end cap 32 is a plastic material (e.g., polycarbonate or the like) over-mold cap that engages portions of the sleeve 28 such that the end of the support rod 16, 18 is completely encapsulated by the end cap 32 (e.g., edges of the core 26 and the sleeve 28 are not exposed due to the end cap 32). Also, the plastic over-mold chemically adheres to the sleeve 28 and the core 26 and is also received within the notches 30 of the sleeve 28 to provide a mechanical interlock between the support rod 16, 18 and the end cap 32. In other embodiments, the end cap 32 can be coupled to the support rod 16, 18 in a different manner (e.g., a snap-fit connection, a threaded connection, etc.).

Figure 7:
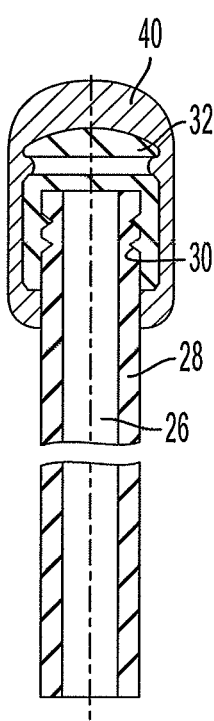
FIG. 7 is a partial cross-sectional view of the support rod and the end cap of FIG. 6 including a support member coupled to the end cap.
Figure 16:
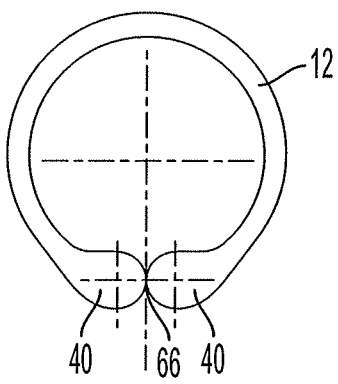
FIG. 16 is a front view of the support member of FIG. 11 in a looped configuration.

The support member 12 is a loop having a pair of connection ends 40 (FIG. 16). As shown in FIG. 7, a connection end 40 of the support member 12 (or support ring) is coupled to the end cap 32 and the sleeve 28 to couple the support member 12 to the second end of the support rod 16, 18. In the illustrated embodiment, the support member 12 is manufactured from medical-grade silicon, and the silicon is over-molded onto the end cap 32 and the sleeve 28. In particular, the polycarbonate end cap 32 and the silicon support member 12 provide a strong chemical adhesion during the over-molding process to secure the support member 12 on the support rod 16, 18. The mechanical interlock between the end cap 32 and the support rod 16, 18 also ensures the support member 12 is secured to the support rod 16, 18. Silicon provides a material that is soft by contact, flexible, stretchable and non-allergenic. In further embodiments, the base ring 22 may be formed from medical-grade silicon as well or a medical-grade plastic.

Figure 8:
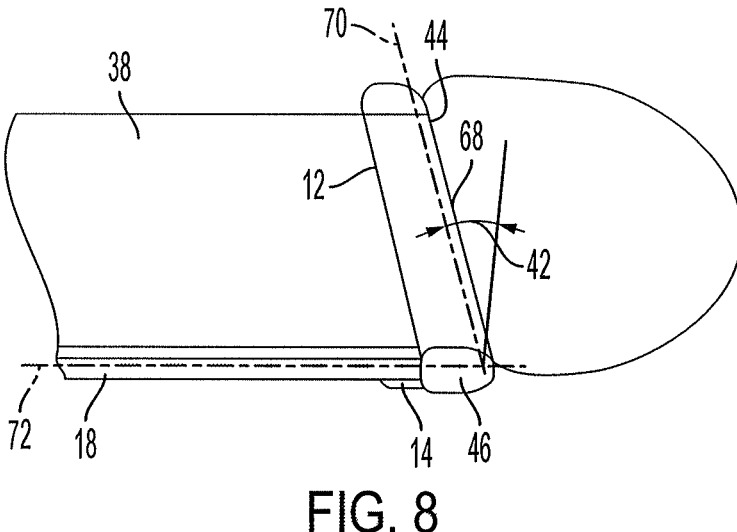
FIG. 8 is a partial side view of the EPSD of FIG. 1 including the support member coupled to a penis.
Figure 10:
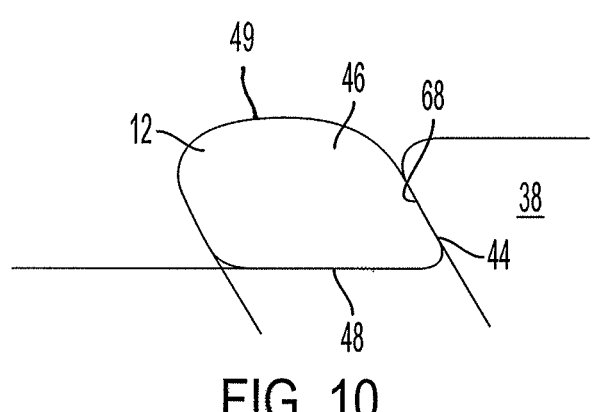
FIG. 10 is a partial cross-sectional view of the support member of FIG. 8 illustrating an interface between the support member and a penis according to another embodiment.

FIG. 8 illustrates the support member 12 coupled to a penis 38. The illustrated support member 12 includes a front surface that is oriented at an oblique, angle 42 relative to an axis 70 that is perpendicular to a longitudinal axis 72 of the support rods 16, 18. A front surface 68 of the support member 12 is planar and abuts a ridge 44 of the penis 38 (FIG. 10). With continued reference to FIG. 10, a non-circular cross section 46 of the support member 12 includes a flat or planar contact surface 48 that abuts a shaft of the penis. An opposite, outer surface 49 of the cross section 46 is curved. The illustrated cross section 46 is generally trapezoidal (with the curved outer surface 49) to evenly distribute pressures created by the support member 12 to the penis shaft (e.g., through the contact surface 48 and the front surface 68 that abuts the ridge 44) to increase comfort when wearing the EPSD 10. In addition, the illustrated cross section 46 aids in preventing the support member 12 from slipping off the penis during intercourse. Furthermore, the illustrated cross section 46 (as well as the material of the support member 12) allows for appropriate expansion and contraction of the support member 12 to accommodate fluctuation in penis sizes due to different degree of blood engorgement of the penis without strangulation of the penis.

Figure 9:
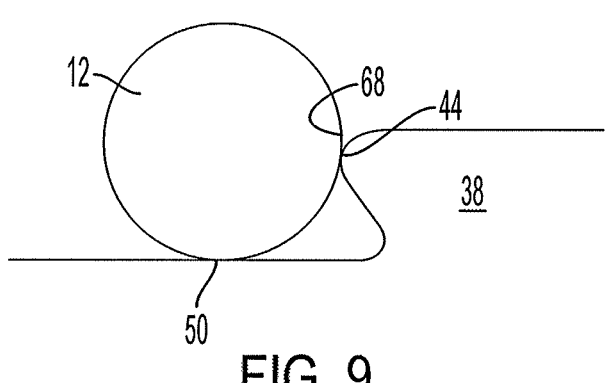
FIG. 9 is a partial cross-sectional view of the support member of FIG. 8 illustrating an interface between the support member and a penis according to one embodiment.

FIG. 9 illustrates another cross section of the support member 12 according to another embodiment. The support member 12 as shown in FIG. 9, has a generally round cross section and includes an arcuate contact surface 50 between the support member 12 and the penis 38. The arcuate contact surface 50 (FIG. 9) provides less contact area between the support member 12 and the penis 38 than the non-circular cross section 46 (FIG. 10). The arcuate contact surface 50 requires application of a significantly higher pressure to the penis shaft than the non-circular cross section 46 in order to provide sufficient retention of the support member 12 on the penis and prevent slippage of the support member 12 from the penis shaft during intercourse. The higher pressure could lead to strangulation of the penis shaft and numbness of the penis if prolong intercourse takes place. As such, the cross section 46 of the support member 12 aids in securing the support member 12 to the penis 38 better than the arcuate contact surface 50 and requires less pressure to provide retention on the penis 38.

With reference to FIG. 11, the connection ends 40 of the support member 12 are coupled to the support rods 16, 18 with the support rods 16, 18 spaced apart such that the support member 12 is in a generally flat configuration. In this configuration, at least the front surface of the support member 12 includes a curvature to provide the desired anatomical angle 42 (FIG. 8) with a corona sulcus of the penis, in particular, an apex 52 of the front surface is axially positioned along the longitudinal axis relative to an end 54 of the connection end 40 by distance 56, such that the angle 42 is defined between a line connecting the apex 52 and the end 54 and a horizontal line through the distance 56. The support member 12 can be manufactured from a flat piece of silicon to simplify the manufacturing process, which also decreases costs of manufacturing the support member 12.

The illustrated slidable lock 14 is coupled to the support rods 16, 18 and is slidable along the support rods 16, 18 to adjust the tension or tightness of the support member 12 on the penis. Prior to attachment of the EPSD 10 to the penis 38, the slidable lock 14 is positioned remote of the support member 12 such that the support rods 16, 18 can be spread apart and the loop 12 opened to facilitate attachment of the EPSD 10 to the penis 38. As shown in FIG. 12, the slidable lock 14 can be slide forward such that a forward surface 61 abuts the connection ends 40 of the support member 12 (e.g., to provide a maximum tension or tightness of the support member 12 on the penis). The illustrated slidable lock 14 includes a thickness less than a thickness of the connection ends 40 (FIG. 12).

During intercourse, an amount of lubricant 58 that naturally occurs or artificially added accumulates behind the connection ends 40, and is greater than a layer of lubricant 60 that forms on the connection ends 40. In other words, the connection end 40 extends further in a direction perpendicular to the support rods 16, 18 than the slidable lock 14. As such, the buildup of lubricant 58 allows for decrease in contact between a partner's skin (e.g., a vagina) and the slidable lock 14 to decrease a sensation of using the EPSD 10. In addition, a surface 62 (FIG. 13) or a rear side of the slidable lock 14 is angled relative to the support rods 16, 18 and the forward surface 61 to provide an inboard surface of the slidable lock 14 that provides maximum contact with the penis shaft (FIG. 8) and an outboard surface 58 of the slidable lock 14 that provides minimal contact with the partner's skin during use of the EPSD 10.

Figure 15:
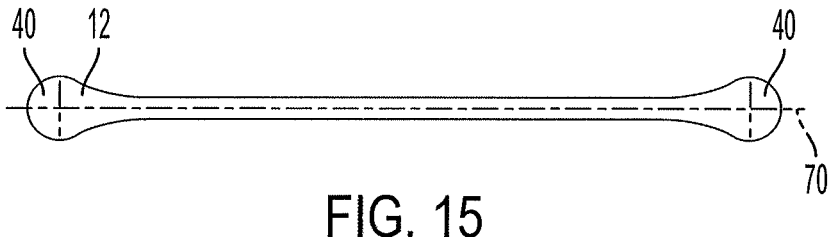
FIG. 15 is a front view of the support member of FIG. 11 in the generally flat configuration.

FIG. 14 illustrates the outboard side (e.g., a bottom side) of the slidable lock 14. The slidable lock 14 includes two cylindrical holes 64 for the support rods 16, 18 to pass through the slidable lock 14. FIG. 15 is a front view of the support member 12 in the generally flat configuration. In the illustrated embodiment, the support member 12 or loop is manufactured in a flat position. FIG. 16 is a front view of the support member 12 after assembly where the support member 12 forms an expandable loop. The support member 12 includes an expandable diameter that varies according to the diameter of the penis 38. Since the support member 12 is made from silicon, the support member 12 can be easily wrapped around the penis during assembly. In addition, the two end connections 40 can abut in the looped configuration (without a gap 66 therebetween; FIG. 16) to avoid pinching between the penis and the end connections 40.

Figure 17:
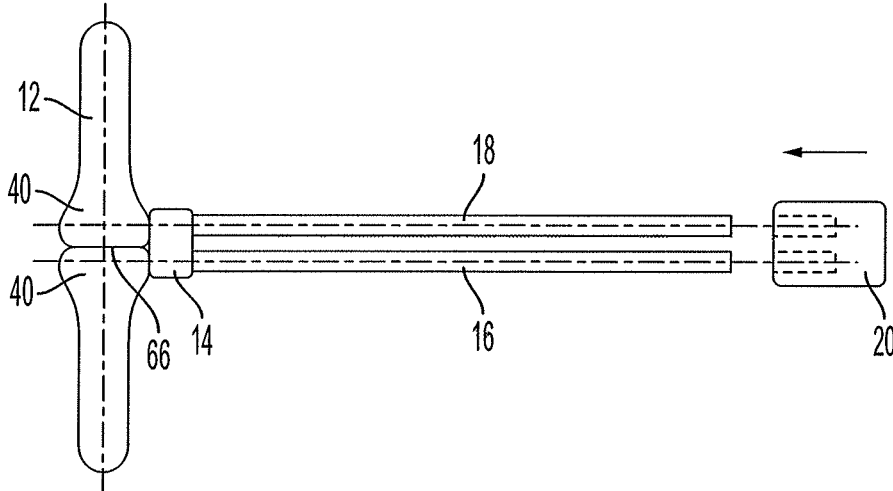
FIG. 17 is a bottom view of the EPSD of FIG. 1.

FIG. 17 illustrates assembly of the EPSD 10. The support member 12 is coiled in such a way that the connection ends 40 abut each other without any gap 66, as described above. The slidable lock 14 is coupled to the support rods 16, 18 and can be slid adjacent the support member 12. The latch 20 is then coupled to the distal ends of the support rods 16, 18. In some embodiments, the latch 20 can be coupled to the support rods 16, 18 by an injection molding process, adhesive process, radio frequency welding process, or the like. A suitable latch is shown and described in U.S. Pat. No. 8,394,011, the entire contents of which is incorporated herein by reference. For example, the latch 20 of the EPSD 10 may be over-molded onto the distal ends of the support rods 16, 18 to provide a pivotable interface with the base ring 22. The latch 20 may include a body having a front support over-molded onto the distal ends of the support rods 16, 18 and a retaining recess generally opposite the front support to pivotally receive, and retain, at least a portion of the base ring 22, for example, by a snap fit or a pin, retention member, and the like. In yet another construction, the latch 20 may include a locking member (not shown) to lock the base ring 22 in place with respect to the body of the latch 20.

As shown in FIGS. 1-3, the base ring 22 is placed near the base of the penis to "anchor" the EPSD 10 during operation. The support structure 24 is then attached to the base ring 22 via the latch 20 such that the support member 12 is positioned adjacent the ridge 44 of the penis 38 and the support rods 16, 18 support the shaft of the penis 38. As discussed above, the slidable lock 14 is slidable along the support rods 16, 18 to adjust the tension of the support member 12 on the penis 38.

A suitable base ring is shown and described in U.S. Pat. No. 8,394,011, the entire contents of which is incorporated herein by reference. For example, the base ring 22 may include an inner core typically formed of plastic having an arcuate portion and a linear portion, and a jacket encompassing at least a portion of the inner core. More specifically, the arcuate portion of the inner core includes an inner diameter substantially corresponding to the diameter of the base of the penis, and the linear portion of the inner core is configured to be at least partially received by and pivotable with respect to the latch 20. The linear portion may also include a plurality of flat surfaces (not shown) corresponding to predetermined positions between the base ring 22 and the latch 20.

During intercourse, the expandable support member 12 easily flexes to increase or decrease in diameter in response to a diameter of a penis increasing or decreasing. The silicon support member 12 provides a soft feel for enhanced comfort to both individuals during use. In addition, the support member 12 is maintained coupled to the penis by at least the cross-sectional geometry 20 of the support member 12 (FIG. 10). Furthermore, the resilient support rods 16, 18 provide sufficient rigidity for penetration and allows movement (e.g., bending, etc.) of the penis during intercourse.

In other embodiments, the EPSD 10 may include a support attachment having two support rings in place of the base ring 22, as shown and described in U.S. Pat. No. 8,394,011, the entire contents of which is incorporated herein by reference. When installed on an EPSD 10, the support attachment reinforces support rods 16, 18 and provides additional stiffening support to the penis when compared to using only the base ring 22.

In yet other embodiments, the EPSD 10 may include a sliding attachment that serves as a compensation device to overcome discrepancy in sizes of genitalia between males and females, as shown and described in U.S. Pat. No. 8,394,011, the entire contents of which is incorporated herein by reference. In other words, the sliding attachment may act as a non-surgical alternative for penis enlargement. The sliding attachment includes a base having a first and a second channel, each corresponding to a respective support rod 16, 18, and a compensation ring extending from the base to substantially encompass a portion of the penis. The sliding attachment is positionable along the length of the support rods 16, 18 during intercourse to provide the feel of an enlarged penis diameter.

Although the disclosure has been described in detail with reference to certain preferred embodiments, variations and modifications exist within the scope and spirit of one or more independent aspects of the disclosure as described.

What is claimed is:

1. An expandable external penile support device for using on a penis having a base, a distal end, and a variable diameter, the expandable external penile support device comprising:

a base ring configured to be positioned adjacent the base of the penis;

a latch coupled to the base ring; and a support structure removably coupled to the base ring by the latch, the support structure, a support member engageable with the distal end of the penis and having an expandable diameter that varies according to the diameter of the penis, the support member also including at least one connection end, at least one support rod extending between the latch and the support member, each of the at least one support rods including a resilient core having a first end proximate the latch and a second end proximate the support member, a sleeve surrounding at least the second end of the resilient core, an end cap engaged with the sleeve such that the end cap encapsulates the second end of the resilient core, wherein the end cap is coupled to the connection end of the support member, wherein an external surface of the sleeve includes a mechanical interlock for coupling the end cap to the sleeve.

2. The expandable external penile support device of claim 1 wherein the support member includes a first planar surface configured for engaging the penis and a second curved surface opposite the first surface.

3. The expandable external penile support device of claim 1 wherein the support member includes a first connection end and a second connection end and the support structure includes a pair of support rods extending between the latch and the support member, each of the support rods connected to one of the first and second connection ends.

4. The expandable external penile support device of claim 1 wherein the mechanical interlock includes a plurality of notches formed on the external surface of the sleeve.

5. The expandable external penile support device of claim 1 wherein the sleeve is over molded to the core.

6. The expandable external penile support device of claim 1 wherein the connection end of the support member is over molded to the end cap.

7. An expandable external penile support device for using on a penis having a base, a distal end, and a variable diameter, the expandable external penile support device comprising:

a base ring configured to be positioned adjacent the base of the penis;

a pair of resilient rods, each having a first end and a second end, the base ring removably coupled to the first ends of the support rods;

a support member configured to engage with the distal end of the penis and having an expandable diameter that varies according to the diameter of the penis, the support member having a first connection end coupled to the second end of one of the resilient rods and a second connection end coupled to the second end of the other of the resilient rods; and a lock member slidably supported by the resilient rods to adjust tension of the support member on the penis, wherein the each of the first and second connection ends includes a bottom surface defining a first plane and the lock member includes a bottom surface defining a second plane, and further wherein the second plane is recessed from the first plane, and wherein the lock member includes a forward surface configured for engaging the support member and a rear surface opposite the forward surface that is angled relative to the forward surface.

8. The expandable external penile support device of claim 7 wherein the support member is formed from medical-grade silicon.

9. The expandable external penile support device of claim 7, and further comprising a latch for removably coupling the pair of resilient rods to the base ring.

10. The expandable external penile support device of claim 7, wherein each of the resilient rods includes a resilient core having a first end proximate the base ring and a second end proximate the support member, a sleeve surrounding at least the second end of the resilient core, an end cap engaged with the sleeve such that the end cap encapsulates the second end of the resilient core, wherein the end cap is coupled to one of the first and second connection ends of the support member.

11. The expandable external penile support device of claim 10 wherein an external surface of the sleeve includes a mechanical interlock for engaging the end cap to the sleeve.

12. The expandable external penile support device of claim 11 wherein the support member has a cross-sectional profile having non-circular shape, and further wherein the cross-sectional profile defines a first planar surface configured for engaging the penis and a second curved surface opposite the first surface.

13. The expandable external penile support device of claim 10 wherein the lock member includes a first surface configured for engaging the support member and a second surface opposite the first surface that is angled relative to the first surface.

14. The expandable external penile support device of claim 10 wherein the connection end of the support member is over molded to the end cap.

15. An expandable external penile support device for using on a penis having a base, a distal end, and a variable diameter, the expandable external penile support device comprising:

a base ring configured to be positioned adjacent the base of the penis;

at least one resilient support rod having a first end and a second end, the base ring removably coupled to the first end of the at least one resilient support rod;

a support member coupled to the second end of the at least one resilient support rod and configured to engage the distal end of the penis, the support member being a non-metallic member configured to expand in response to the variable diameter of the penis increasing; and a lock member slidably supported by the at least one resilient rod to adjust tension of the support member on the penis, wherein the lock member includes a forward surface configured for engaging the support member and a rear surface opposite the forward surface that is angled relative to the forward surface.

16. The expandable external penile support device of claim 15, wherein the support member includes a bottom surface defining a first plane and the lock member includes a bottom surface defining a second plane, and further wherein the second plane is recessed from the first plane.

17. The expandable external penile support device of claim 15 wherein the support member is an expandable loop having a cross-section profile with a non-circular shape, and further wherein the cross-sectional profile defines a bottom surface that is planar and configured for engaging the penis and a second surface that is curved and opposite the first surface.

* * * * *